US00PP24805P3

(12) United States Plant Patent
Warner

(10) Patent No.: US PP24,805 P3
(45) Date of Patent: Aug. 26, 2014

(54) SHRUB ROSE PLANT NAMED 'CHEWSUMSIGNS'

(50) Latin Name: *Rosa hybrida*
Varietal Denomination: CHEwsumsigns

(71) Applicant: Texas Rose Ventures, Waddell, AZ (US)

(72) Inventor: Christopher Hugh Warner, Shropshire (GB)

(73) Assignee: Texas Rose Ventures, Waddell, AZ (US)

( * ) Notice: Subject to any disclaimer, the term of this patent is extended or adjusted under 35 U.S.C. 154(b) by 81 days.

(21) Appl. No.: 13/694,233

(22) Filed: Nov. 9, 2012

(65) Prior Publication Data
US 2014/0137301 P1 May 15, 2014

(51) Int. Cl.
*A01H 5/00* (2006.01)

(52) U.S. Cl.
USPC ..... Plt./102

(58) Field of Classification Search
USPC ..... Plt./102, 107
See application file for complete search history.

*Primary Examiner* — Kent L Bell
(74) *Attorney, Agent, or Firm* — McKee, Voorhees & Sease

(57) ABSTRACT

A new variety of Shrub rose suitable for garden decoration, having flowers of light pink coloration with a distinctly darker eyezone.

1 Drawing Sheet

Classification: The present invention relates to a new *Rosa hybrida* plant.

Variety denomination: The new plant has the varietal denomination 'CHEwsumsigns'.

BACKGROUND OF THE INVENTION

This invention relates to a new and distinct variety of Shrub Rose. It has as its seed parent the variety known as 'KORizont' (not patented) and as its pollen parent an undisseminated seedling of my creation.

SUMMARY OF THE INVENTION

Among the features which distinguish the new variety from other presently available and commercial rose cultivars known to the inventor are the following combinations of characteristics: its soft pink single flowers with a distinct darker pink eyezone, its dark coloration at the base of the filaments, its red coloration on the hypanthium at the point where the filaments attach and its predominance of seven leaflet leaves. The plant has a bushy somewhat spreading plant growth habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'CHEwsumsigns' may be asexually propagated by budding and grafting. The budding and grafting successfully occurred on the plant/rootstock *Rosa hybrida* cv. Dr. Huey (not patented).

COMPARISON WITH PARENTS

The new rose may be distinguished from its seed parent, KORizont, by the following combination of characteristics: whereas the seed parent bears medium-large (about 7.5 to about 9 cm. in diameter) semi-double flowers of about 8 to about 10 petals, 'CHEwsumsigns' bears significantly smaller (about 5.5 to about 6.2 cm. in diameter) single flowers mostly with 5 petals. Whereas the new variety bears flowers of soft pink coloration with a distinctly darker pink eyezone, 'KORizont' bears flowers of more uniform orange pink coloration with no darker eyezone. Whereas 'CHEwsumsigns' is a Shrub with a bushy slightly spreading habit, the seed parent is classified as a Climber with a significantly larger more spreading climbing habit.

The new variety may be distinguished from its pollen parent, an undisseminated seedling of my creation, by the following combination of characteristics: whereas the pollen parent is classified as a Floribunda with a very compact growing habit, 'CHEwsumsigns' is classified as a Shrub with a significantly larger and more spreading plant habit. Whereas the new variety bears medium-small (about 5.5 to about 6.2 cm. in diameter) single petaled flowers mostly with 5 petals, the pollen parent bears significantly larger (about 8 to about 10 cm. in diameter) semi-double flowers with about 10 to about 12 petals. Whereas 'CHEwsumsigns' bears light pink flowers with a distinctly darker pink eyezone, the undessiminated pollen parent bears deep pink flowers with a less distinguishable deep pink eyezone.

COMPARISON WITH THE CLOSEST COMMERCIALLY AVAILABLE CULTIVAR

The new variety may be distinguished from its closest commercially available cultivar, 'MORglory' (not patented) by the following combination of characteristics: whereas 'MORglory' is classified as a Miniature with small flowers (about 3.8 to about 4.6 cm. in diameter) of semi-double petalage (about 5 to about 10 petals), 'CHEwsumsigns' is classified as a Shrub, bearing significantly larger single flowers (about 5.5 to about 6.2 cm. in diameter) with significantly less petals (only 5). Whereas 'CHEwsumsigns' bears flowers of soft pink coloration with a darker pink eyezone, 'MORglory' bears flowers of a significantly darker pink coloration with a darker eyezone and a lighter colored petal reverse.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 2 year-old rose plants of the new variety grown outdoors in Kern County, Calif. in the month of October. Phenotypic expression may vary with environmental, cultural and climatic conditions, as well as differences in conditions of light and soil.

FLOWER

The new variety usually bears its flowers in clusters of five or more per stem. Flowers may be borne in irregular somewhat rounded to pyramidal clusters on moderately pendulous medium long stems (about 26 to about 42 cm.). Outdoors, the plant blooms abundantly and nearly continuously during the growing season. The flowers have a slight spicy fragrance.

BUD

The peduncle is about 2.3 to about 3.2 cm. in length, of average caliper (about 0.2 to about 0.3 cm. in diameter), and usually erect. It is moderately smooth, with some stipitate glands and few hairs near the top. Peduncle color is between 146B and 144A sometimes moderately suffused, especially on the side exposed to the sun, with near 183B.

Before the calyx breaks, the bud is about 1.0 to about 1.2 cm. in diameter at the widest point, about 1.6 to about 1.9 cm. in length, and very pointed to ovoid in shape. The surface of the bud bears few stipitate glands, usually with slender entire foliaceous parts extending beyond the tip of the bud about ¼ to ½ of its length. Bud color is between 146A and 138A sometimes moderately suffused, especially on the side exposed to the sun, with near 183B.

The sepals are about 1.6 to about 2.2 cm. in length and about 0.5 to about 0.6 cm. in width at the widest point. The outer surface color of the sepal is between 138A and 146A, sometimes moderately suffused, especially on the side exposed to the sun, with near 183B. The outer surface of the sepal is moderately smooth and bears between 1 to 4 foliaceous appendages with few stipitate glands. The inner surface color of the sepal is near 138B. The inner surface of the sepal is covered with fine wooly tomentum; sepal margins are lined with few stipitate glands and some hairs.

The receptacle of the flower is of moderately short length (about 0.4 to about 0.7 cm.) and average in caliper (about 0.5 to about 0.6 cm. in diameter). The receptacle is somewhat globular in form. Its surface is somewhat smooth with few stipitate glands and moderately thin fleshy walls. The receptacle color is between 138A and 146A sometimes lightly suffused, especially on the side exposed to the sun, with near 183B.

As the petals open (after the calyx breaks), the bud is about 1.2 to about 1.5 cm. in diameter at the widest point, about 1.8 to about 2.2 cm. in length, and very pointed to ovoid in form. The color of the under surfaces of the newly opened petals is between 55A and 58B. At the point where the petal attaches, there is a somewhat small zone of near 154D. The color of the upper surfaces of the newly opened petals is between 55B and 58C. At the point where the petal attaches, there is a small zone of near 174A. Surrounding the attachment zone is a moderately larger zone of between 59C and 59B that extends into about ¼ of the petal length.

BLOOM

When fully open, the bloom ranges from about 5.5 to about 6.2 cm. in diameter. Petalage is single with 5 petals, mostly without petaloids. When partially open, the bloom form is somewhat cupped to flat and the petals are somewhat cupped to flat with undulated petal edges. When fully open, the bloom form is more flat and the petals are very flat to slightly undulated with petal edges less undulated to somewhat reflexed outward.

PETALS

The substance of the petals is moderately heavy and of medium thickness, with upper surfaces moderately satiny to velvety and under surfaces more shiny. The petals are about 2.5 to about 2.9 cm. in length and about 2.6 to about 2.9 cm. in width at the widest point. Petal margins are entire. The petals are broadly obovate to nearly round in shape with somewhat rounded apices.

NEWLY OPENED FLOWER

The under surface color of the petals is between 55B and 63C. At the point where the petal attaches, there is a somewhat small zone of near 154D. The upper surface color of the petals is between 55C and 62C, sometimes with a wash of as dark as 63C at the outer part of the petal midrib. At the point where the petal attaches, there is a moderately small zone of near 174B. Surrounding the attachment zone is a moderately larger zone of between 58B and 61C that extends into about ¼ to about ⅓ of the petal length.

The general tonality of the newly opened flower is between 55C and 62D with a darker eyezone of between 58B and 61C.

THREE-DAY-OLD FLOWER

The under surface color of the petals is between 55D and 62C. At the point where the petal attaches, there is a moderately small zone of near 155C. The upper surface color of the petals is between 65D and 62D, sometimes with a wash of as dark as 68C at the outer part of the petal midrib. At the point where the petal attaches, there is a moderately small zone of near 177D. Surrounding the attachment zone is a moderately larger zone of between 61C and 64C that extends into about ¼ to about ⅓ of the petal length.

The general tonality of the three-day-old flower is between 65D and 62D with a darker eyezone of between 61C and 64C.

On the spent bloom, the petals usually drop off cleanly and are not particularly affected by cold, hot, wet, or dry weather.

In October in Kern County, Calif., blooms on the bush growing outdoors generally last about three to four days. Cut roses from plants grown outdoors and kept at normal indoor living temperatures generally last about three to four days.

MALE REPRODUCTIVE ORGANS

Stamens are average to many in number (average about 90) and are arranged regularly about the pistils. The filaments are very irregular in length ranging from short to long (about 0.3 to about 1.1 cm.) most with anthers. Filaments are colored with a small base of between 187A and 187B suffusing to a somewhat small mid-section of near 53B. The remaining majority of the filament is between 21A and 23A in color. At the top of the hypanthium, at the point where the filaments attach, there is a coloration of near 44B. The anthers are moderately small for the class and all open approximately at the same time. Anther color when immature is near 22A. Anther color at maturity is near 163A. Pollen is moderately abundant and near 23C in color.

FEMALE REPRODUCTIVE ORGANS

Pistils vary in number (average about 35). The styles are somewhat short in length (about 0.2 to about 0.4 cm.), thin to average in caliper, and very bunched. Stigma color is near 161C. Style color is near 155A at the base suffusing to near 53B on the upper half. Ovaries are usually all enclosed in the calyx.

Hips are of somewhat short to average length (about 10 to about 12 cm.), very globular in form, and near 169C in color when ripe. The hip surface is very smooth with somewhat thick fleshy walls. The sepals are mostly fugacious.

The seeds are irregularly rounded, smooth in texture, approximately 10 to about 14 per hip, about 0.2 to about 0.3 cm. in diameter at the widest point and near 165D in color.

FOLIAGE

The compound leaves are usually comprised of three to seven leaflets and are borne abundantly. The seven-leaflet leaves are about 10.2 to about 11.8 cm. in length and about 7.8 to about 9.5 cm. in width at the widest point, heavy to somewhat leathery in texture, and very glossy in finish on the upper side and more semi-glossy to matte in finish on the underside. The leaves have a pinnate venation pattern. The terminal leaflets are about 4.1 to about 5.0 cm. in length and about 2.2 to about 3.2 cm. in width at the widest point, shaped somewhat oval to slightly ovate with acute apices and with sometimes round to sometimes inequilateral bases. Their margins are usually simply serrate.

The upper surface color of the mature leaf is between 139A and 146A. The under surface color of the mature leaf is between 138A and 147B. The upper surface color of the young leaf is between 146B and 137C, sometimes heavily suffused with as dark as between 183B and 187C. The under surface color of the young leaf is between 146B and 137C, usually heavily suffused with as dark as between 183B and 187C.

The rachis is average in caliper and somewhat smooth. The upper side is moderately shallowly grooved with few stipitate glands on the edges of the grooves. The under side of the rachis is somewhat more rough with a few stipitate glands and about 1 to about 2 somewhat small prickles. The rachis color is between 146B and 137C.

The stipules are about 1.3 to about 1.6 cm. in length and somewhat narrow (about 0.1 to about 0.2 cm.) with medium long straight points that usually turn out at an angle of more than 45 degrees. The under surface color of the stipule is between 146B and 137C. The upper surface color of the stipule is between 139A and 146A.

The petiole is average in caliper and moderately smooth. The upper side is somewhat shallowly grooved with few stipitate glands. The under side of the petiole is somewhat smooth with a few stipitate glands. The petiole is about 0.1 to about 0.2 cm. in length and about 0.1 cm in width at the widest point. The under surface color of the petiole is between 146B and 137C. The upper surface color of the petiole is between 139A and 146A.

The plant displays an above average degree of resistance to powdery mildew and rust as compared to other commercial varieties grown under comparable conditions in Kern County, Calif. known to the Inventor. The plant's winter hardiness and drought/heat tolerance are yet to be determined.

GROWTH

The plant has a bushy somewhat spreading medium height growth habit (about 95 to about 110 cm. in height and about 130 to about 150 cm. spread at the widest point), with very full branching. It displays very vigorous growth and the canes are of medium to heavy caliper for the class (about 1.8 to about 2.5 cm. in diameter at the widest point).

The color of the major stems is between 146C and 148B. They bear several large prickles that are about 0.5 to about 0.8 cm. in length. The large prickles are almost straight and hooked slightly downward with a moderately long narrow oval base; prickle color is between 166A and 167A. The major stem bears few small prickles of similar shape and coloration.

The color of the branches is between 144A and 137C. They bear several large prickles which are of similar size and shape to the large prickles on the major stems; prickle color is between 163A and 166B. The branches bear some small prickles of similar shape and coloration.

The color of the new shoots is between 144A and 146C usually heavily suffused with as dark as between 183B and 187C. They bear many large prickles which are of similar size and shape to the large prickles on the major stems; prickle color is between 183A and 187B. The shoots bear several small prickles of similar shape and coloration.

I claim:

1. A new and distinct Shrub rose plant of the variety substantially as described and illustrated herein.

* * * * *

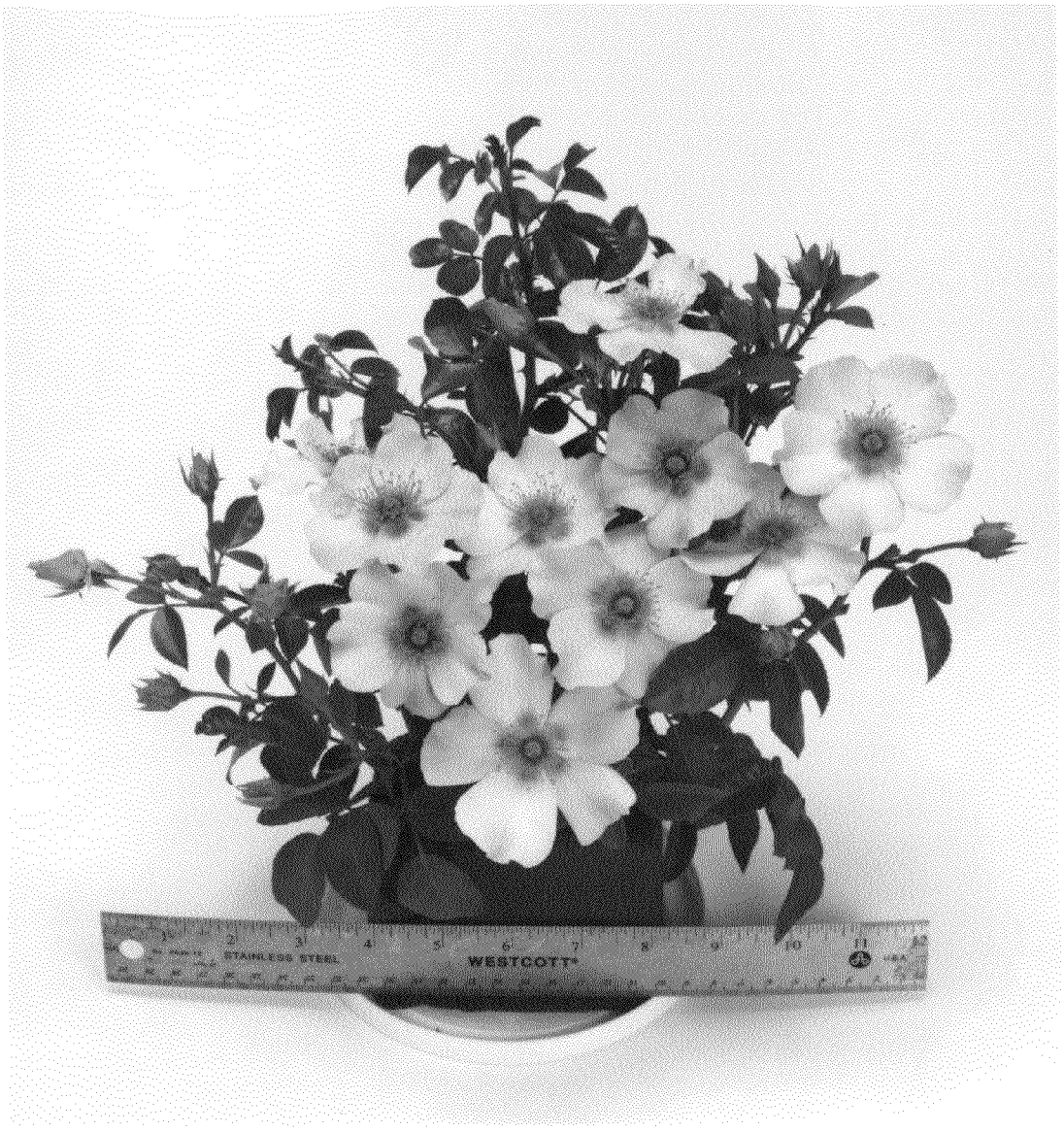
STAINLESS STEEL
WESTCOTT